My

United States Patent [19]

Egan

[11] 3,986,349

[45] Oct. 19, 1976

[54] METHOD OF POWER GENERATION VIA COAL GASIFICATION AND LIQUID HYDROCARBON SYNTHESIS

[75] Inventor: Clark J. Egan, Piedmont, Calif.

[73] Assignee: Chevron Research Company, San Francisco, Calif.

[22] Filed: Sept. 15, 1975

[21] Appl. No.: 613,654

[52] U.S. Cl. .......................... 60/39.02; 260/449.6; 260/449 R; 60/39.18 B
[51] Int. Cl.[2] ........................................ F02B 43/08
[58] Field of Search ......... 60/39.02, 39.12, 39.46 R; 260/449 M, 449.6

[56] References Cited
UNITED STATES PATENTS

| | | | |
|---|---|---|---|
| 2,472,219 | 6/1949 | Lyons | 260/449.6 |
| 2,649,468 | 8/1953 | Benedict et al. | 260/449.6 |
| 2,838,388 | 6/1958 | Cankeek et al. | 260/449.6 |
| 3,254,023 | 5/1966 | Mialo | 260/449 R |

FOREIGN PATENTS OR APPLICATIONS

| | | | |
|---|---|---|---|
| 518,758 | 11/1955 | Canada | 260/450 |

Primary Examiner—Carlton R. Croyle
Assistant Examiner—L. J. Casaregola
Attorney, Agent, or Firm—G. F. Magdeburger; R. H. Davies; J. J. De Young

[57] ABSTRACT

Disclosed is an integrated process for the generation of power, particularly electrical power, from a solid carbonaceous material. A solid carbonaceous material is gasified to produce a combustible synthesis gas. A first portion of this synthesis gas is contacted with Fischer-Tropsch and hydrogenation catalysts to produce normally liquid hydrocarbons and a second combustible gaseous stream. Portions of the two combustible gaseous streams are combined and combusted and utilized to generate a base-load power output and the liquid hydrocarbons are utilized as a fuel for a gas turbine to produce supplemental power for peak-load demand.

10 Claims, 2 Drawing Figures

METHOD OF POWER GENERATION VIA COAL GASIFICATION AND LIQUID HYDROCARBON SYNTHESIS

BACKGROUND OF THE INVENTION

1. Field of the Invention

This invention relates to the generation of mechanical and/or electrical power. More particularly, this invention relates to a process for the generation of electrical energy from a solid carbonaceous material such as coal, in which a base power load is generated by combusting a gas and supplemental power for peak loads is produced from a gas turbine by combusting a synthetic, normally liquid hydrocarbon. The combustible gas for base-load power production and the normally liquid hydrocarbon used for peak-load power production are both produced in an integrated solid-fuel gasification and hydrocarbon synthesis process.

2. Description of the Prior Art

Solid carbonaceous materials have been used for a long time in the generation of power, particularly electrical energy. Generally coal is combusted with air and the exothermic heat of reaction is used to produce high-pressure steam, and then the steam in turn is expanded through a turbine to generate mechanical or electrical energy. Similarly, natural gas and other gaseous fuels have been combusted to form high-pressure steam for the generation of electrical power.

The electrical industry has developed highly efficient, large generators driven by expanding steam. However, one problem in the generation of electrical power from steam results from the greatly varying demand for electrical energy. Steam generators are not well suited for producing greatly varying amounts of steam, but rather are designed for base-load or constant-load types of operation. To provide for peak-load and reserve-load demands, the open-cycle gas turbines have generally been utilized because of their quick-startup capability and relatively low capital cost. Open-cycle turbines, however, require special fuels which are noncorrosive to the turbine blades. Generally it has been found to be uneconomical to combust coal or residual oils directly in the combustion chamber of a gas turbine, because the fuel contains high amounts of ash and sulfur. Due to the incomplete combustion, such high-ash solid fuels generally produce solid abrasive and corrosive particles. When such particles are entrained in the flue gas that is passed through the turbine, they deposite on the blades and erode the blade surfaces. When this corrosion occurs, the blade is damaged reducing the efficiency of the unit and the passages in the turbine become clogged. Further, the fine particles may deposit down-stream in heat-exchange surfaces and impair thermal efficiency. Similar problems are encountered when burning ash-producing liquid petroleum products. Such ash includes mineral compounds, as those found in crude oil. These compounds are concentrated in the residuals by the refining process and are supplemented by silica, iron, and sodium compounds which are picked up in shipment and in handling. Vanadium, nickel, sodium, sulfur and oxygen are the major components of the ash. After burning, they appear as metallic oxides, sulfates, vanadates and silicates. These compounds appear to erode the protective oxide films of high-temperature alloys used in gas turbines. Oxidation of the turbine blades is thereby accelerated, especially above about 1200° F. Previous methods in which the fuel gas was cleaned prior to being introduced into the gas turbine were either impractical, unduly costly, or both.

The aforesaid problems of base-load and peak-load demand, combined with the special fuel requirements for gas turbines, are substantially avoided by the subject invention, which integrates the production of a base-load power generation combined with the production of a clean, normally liquid fuel which is particularly useful for the generation of peak-load power in an open-cycle gas turbine.

Because coal and other solid carbonaceous materials often contain sulfur compounds, the combustion of coal for power production can also cause serious air pollution problems. Also, because of the greatly expanded volumes of gases produced after combustion, it is very expensive to remove the polluting sulfur compounds after combustion. These sulfur-removal problems and air-pollution problems have led to processes for the gasification of coal to produce a clean fuel gas wherein the sulfur is removed from the fuel prior to combustion. One problem, however, with such gasification processes is that only a low-Btu-value gas is produced, and it is generally not economical to transport a low-Btu-value gas over great distances. This has led to proposals for large on-site or "mine-mouth" gasification and power generation plants where the low-Btu-value gas is immediately converted to electrical power for transmission. Such on-site gasification and power generation processes solve the problem of low-Btu-gas transportation and sulfur-removal problems, but such gasification processes are not economical for producing greatly varying amounts of fuel as is needed for peak-load generation of power, either because it is too expensive to store gaseous products for subsequent use in gas turbines or because the capital expense of providing for greatly increasing the gas production rate and gas cleanup rate for peak-load demand is uneconomical.

The aforesaid problems are substantially avoided by the subject invention, which process provides for base-load and peak-load power demand. The process integrates the production of a combustible fuel gas for base-load power generation with a process for producing normally liquid hydrocarbons which are free of sulfur and other impurities and which are suitable for storage and use for peak-load power generation using a gas turbine.

U.S. Pat. No. 3,868,817 discloses a process for the generation of mechanical and electrical power from a purified fuel gas produced from solid carbonaceous fuels. The purified fuel gas is used to generate power using gas turbines.

As described in the report entitled "New Fossil Fuel Power Plant Processes based on Lurgi Pressure Gasification of Coal" by Paul F. H. Rudolph, delivered at ACS (American Chemical Society) on May 27, 1970, coal-burning gas turbines are used at Lunen in West Germany to drive electricity generators. As disclosed in that report, carbon or coal can be gasified in the presence of oxygen and $H_2O$. Gases from the gasification zone are purified to remove coal dust and fly ash, and also many other impurities such as vaporized ash, alkali and chlorine which are detrimental to the operation of gas turbines. After purification of the gases from the gasification step, the gases are then combusted with air and then expanded through a gas turbine, which turbine is used to drive an electricity generator. The Rudolph report is directed to the gasification of coal and other similar materials with the subsequent purification and combustion of the gasification products. The Rudolph report does not disclose a gasification process followed by Fischer-Tropsch hydrocarbon synthesis and hydrogeneration steps to produce liquid fuels particularly useful for generating power using gas turbines for peak-load demand.

Similar coal gasification and power generation processes are disclosed in U.S. Pat. Nos. 2,735,265 and 2,718,754.

The Fischer-Tropsch synthesis was used extensively in Germany during World War II to produce gasoline-boiling-range hydrocarbons. Today the Fischer-Tropsch synthesis is still being used commercially in South Africa, to produce straight-chain, high-boiling-range hydrocarbons with some medium-boiling oils, diesel oil, L-P gas, and oxygenated compounds. The existing commercial facilities using the Fischer-Tropsch process are detailed in a series of 4 articles by J. C. Hoogendoorn and J. M. Solomon, "Sasol: World's Largest Oil-From-Coal Plant", British Chemical Engineering, Part 1, May 1957, page 238; Part 2, June 1957, page 308; Part 3, July 1957, page 368; Part 4, August 1957, page 418.

SUMMARY OF THE INVENTION

A process is disclosed for the generation of power from a solid carbonaceous material which comprises:

a. forming a combustible synthesis gas by reacting said carbonaceous material with steam and oxygen at an elevated temperature;

b. passing a first portion of said synthesis gas into a reaction zone containing a hydrocarbon synthesis catalyst and a hydrogenation catalyst and forming a reaction product mixture containing water, $H_2$, CO, $CO_2$ and synthetic hydrocarbons;

c. separating from said reaction product mixture a gaseous first fraction comprising $H_2$, CO, $CO_2$ and light hydrocarbons, a second fraction comprising normally liquid hydrocarbons and a third fraction comprising water;

d. combining at least a portion of said first fraction with a second portion of said synthesis gas and combusting said combined gases and generating power from said combusted gases; and e. generating additional power from said liquid hydrocarbons by combusting at least a portion of said hydrocarbons forming a flue gas and passing said flue gas through an expansion turbine as the working fluid.

DETAILED DESCRIPTION OF THE INVENTION

Figure 1:
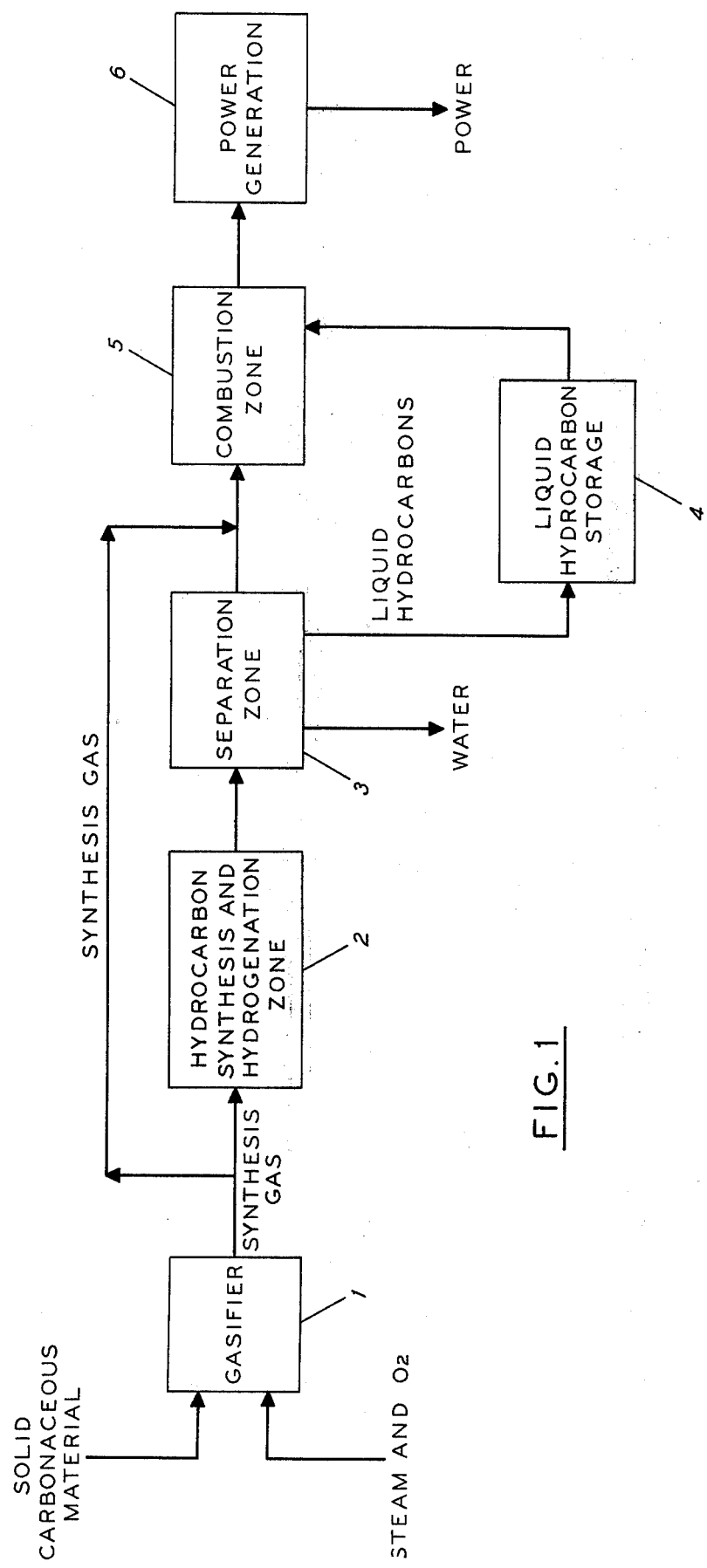
FIG. 1 is a schematic flow diagram illustrating the broad concept of the present invention.

Referring to FIG. 1, a solid carbonaceous material such as coal, coke, peat, municipal or agricultural wastes, etc., is contacted with steam and a free- or elemental-oxygen-containing gas in gasifier 1 to produce a synthesis gas containing $H_2$ and CO. A first portion of the synthesis gas is fed into reaction zone 2, which contains hydrocarbon synthesis and hydrogenation catalysts. The term "hydrocarbon synthesis catalyst" as used herein means those metals or compounds which catalyze or promote the reaction of $H_2$ and CO to form hydrocarbons. These hydrocarbon synthesis catalysts are commonly known as Fischer-Tropsch catalysts. The term "hydrogenation catalyst" as used herein is meant to include catalysts which exhibit hydrogenation activity and also includes other catalysts which are multifunctional, for example, hydrocracking catalysts which exhibit both hydrogenation and cracking activity. In reaction zone 2, the synthesis gas is contacted with the catalysts to form a reaction product containing water, $H_2$, CO, $CO_2$, light hydrocarbons such as methane, ethane, propane and butane, and normally liquid hydrocarbons having carbon numbers in the range $C_5$–$C_{22}$ or higher. The term "normally liquid" is used herein to mean hydrocarbons boiling at the same temperature or higher than $C_5$ hydrocarbons. In separation zone 3, the reaction zone 2 products are separated into a first fraction comprising $H_2$, CO, $CO_2$ and light gaseous hydrocarbons, a second fraction comprising normally liquid hydrocarbons, and a third fraction comprising water. The first fraction from the separation zone is then combined with a portion of the synthesis gas from gasifier 1 and combusted in combustion zone 5. Power is generated from the combusted gas in zone 6 either directly by expansion of the combusted gases through a gas turbine or indirectly, for example, by generation of steam and expansion of the steam through a turbine. The normally liquid hydrocarbons from separation zone 3 are stored, 4, and combusted as needed to generate additional power for peak-load power demand.

Figure 2:
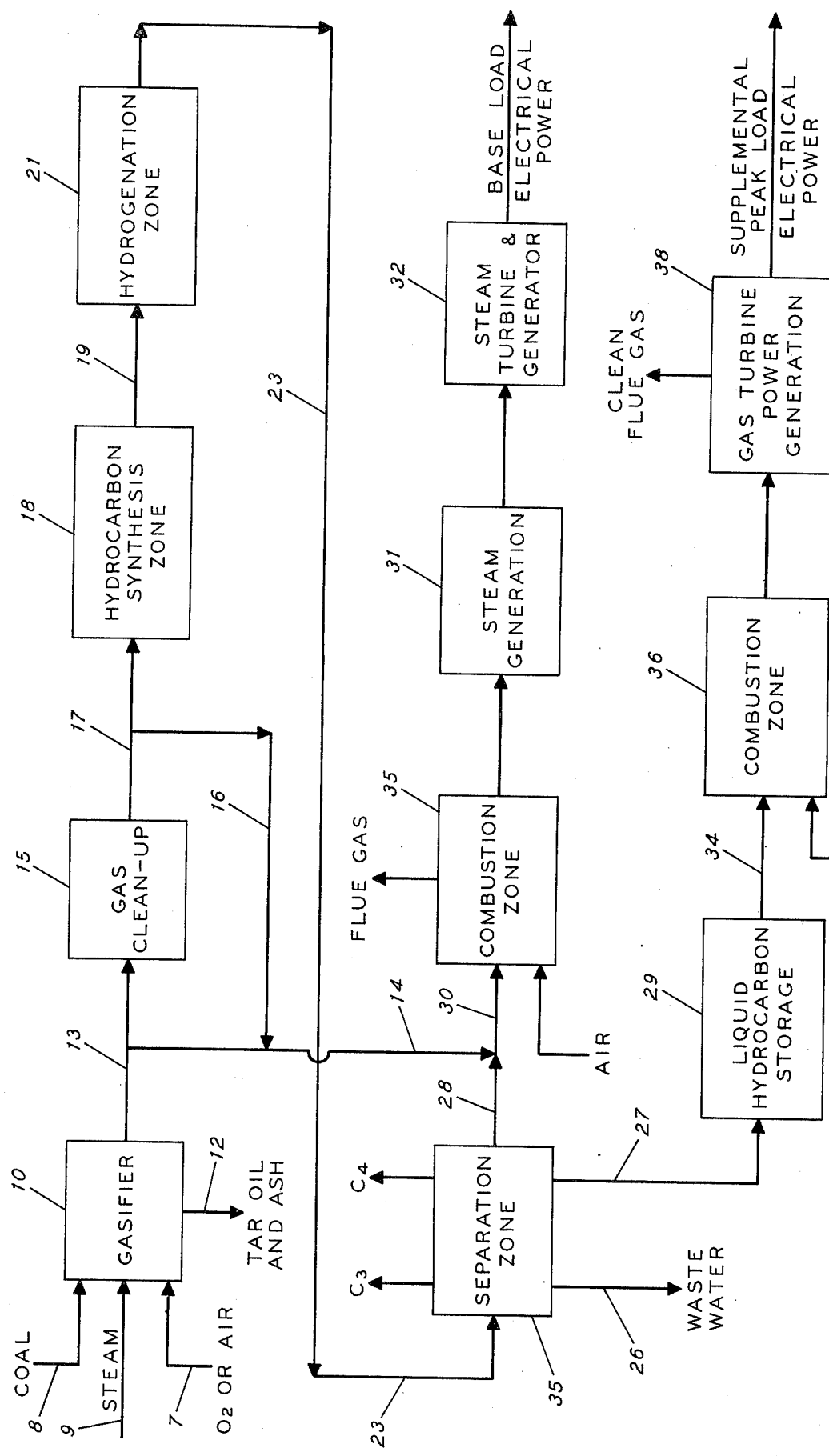
FIG. 2 is a schematic flow diagram illustrating a more preferred embodiment of the present invention.

Now referring to FIG. 2, which illustrates a more detailed, preferred embodiment of the invention, coal or some other solid carbonaceous material is fed to gasifier 10 via line 8 and contacted with steam and oxygen fed into the reaction zone via lines 7 and 9. The gasifier produces a synthesis gas, 13, and, in addition to containing $H_2$ and CO, the gas will also contain $CO_2$, $H_2O$, $NH_3$, sulfur compounds such as $H_2S$, and light hydrocarbons, particularly methane. Tar oil, ash, and coal dust are removed via line 12.

Any of the numerous commercially available gasification processes can be utilized, for example the Lurgi or the Kopper-Totzek processes. Preferably a gasification process is utilized which produces an $H_2$/CO ratio of 0.75 to 3 or more preferably 1 to 2. For this reason, the Lurgi gasifier is preferred. The operation of the Lurgi gasifier is described, for example, in "The Oil and Gas Journal", Jan. 22, 1973, pp. 90–93, the disclosure of which is incorporated herein by reference. A portion of the synthesis gas is then fed via lines 14 and/or 16 to combustion zone 35.

A portion of the crude gas is passed via line 13 to purification zone 15. The crude gas purification system removes the $NH_3$, $CO_2$, $H_2S$, $SO_2$, COS and other impurities to produce a purified synthesis gas containing essentially only methane $H_2$ and CO. The purified synthesis gas must be essentially free of sulfur compounds, i.e., less than 5 ppm and preferably less than 0.1 ppm, in order to prevent poisoning of the down-stream Fischer-Tropsch catalyst. The purification zone will preferably comprise a Rectisol-type purification systm as is well known in the art. A preferred gas purification system is described in the aforementioned "Oil and Gas Journal" of Jan. 22, 1973.

The synthesis gas enters hydrocarbon synthesis zone 18 via line 17. The ratio of $H_2$ to CO may be in the range 1/1:3/1, with 2:1 being particularly preferred. The ratio of $H_2$ and CO can readily be adjusted within the desired range by varying the reaction conditions in gasifier 10 or by the insertion of a shift conversion step or by utilizing makeup $H_2$ or CO from some other source.

In hydrocarbon synthesis zone 18 the $H_2$ and CO are contacted with a Fischer-Tropsch catalyst to produce synthetic hydrocarbons. The Fischer-Tropsch catalyst and reaction conditions are well known in the art. Typical Fischer-Tropsch catalysts useful in the process of the present invention are in general the cobalt, nickel, iron and ruthenium-containing Fischer-Tropsch catalysts as taught in "Fischer-Tropsch and Related Synthesis", by H. H. Storch et al., John Wiley and Sons, New York, N.Y. (1951). Particularly preferred is an iron-copper catalyst.

Typical Fischer-Tropsch process conditions useful in the present invention include a temperature in the range 400°–800° F, a pressure in the range 15–600 psig and a feed gas having an $H_2$:CO ratio of about 1/1:3/1, with a preferred feed ratio of $H_2$:CO of about 2:1, and feed gas hourly space velocity from 100 to 1000.

Typical products of the Fischer-Tropsch reaction include hydrocarbons from $C_1$–$C_{60}$ or higher, with the bulk of the hydrocarbons produced being in the $C_1$–$C_{50}$ range. Typically from 40 to 80% of the hydrocarbons produced are straight-chain olefins and paraffins. The Fischer-Tropsch reaction also produces varying amounts of water, $CO_2$ and oxygenated components, including acids such as acetic acid, formic acid, propionic acid; alcohols such as methyl, ethyl and propyl alcohol; aldehydes, ketones and esters. Typically these oxygenated components comprise 1 to 20 weight percent of the Fischer-Tropsch reaction product.

The total reaction product effluent from the hydrocarbon synthesis zone is fed via line 19 to hydrogenation zone 21. The Fischer-Tropsch reaction product is fed to the hydrogenation zone prior to formation of an aqueous phase, so as to avoid the severe corrosion problems and waste-water treatment problems normally associated with Fischer-Tropsch processes in which the Fischer-Tropsch reaction product is cooled and the water and oxygenated components, particularly acids, phase-separate from the hydrocarbon products. This aspect of the invention of passing the total Fischer-Tropsch reaction product prior to the formation of an aqueous phase to a hydrogenation or hydrocracking zone is more fully described in my copending application entitled "Hydrocarbon Synthesis Process", filed June 13, 1975, Ser. No. 586,683, the disclosure of which is incorporated herein by reference.

The Fischer-Tropsch process per se is deficient in many aspects for the production of high yields of normally liquid hydrocarbons useful as turbine fuels. More particularly:

1. The Fischer-Tropsch process produces appreciable quantities of high-boiling hydrocarbons, that is, boiling above about 800° F, whereas it is preferred that turbine fuels boil below 800° F and preferably below 600° 8 F.

2. The Fischer-Tropsch process produces appreciable amounts, typically from 1 to 20 weight percent, of oxygenated components, particularly acids, which are not suitable for use as turbine fuels.

Thus, it is desired to produce a normally liquid hydrocarbon product in the hydrocarbon synthesis and hydrogenation reaction zone which:

1. boils in the range useful for turbine fuels, between about 60° and 800° F, and preferably below 600° F, and 2. is essentially free of oxygenated components, particularly acids.

The term "oxygenated components" is used herein to mean molecules containing carbon, hydrogen and oxygen, and the phrase "essentially free of oxygenated components" is used herein to mean the normally liquid hydrocarbon product contains less than 1.0 and preferably less than 0.5 weight percent oxygenated components.

Furthermore, since the feedstock to the Fischer-Tropsch process must be essentially free of sulfur in order to prevent poisoning of the Fischer-Tropsch catalyst, the hydrocarbons obtained from the present invention are essentially free of sulfur contaminants, that is, less than 0.1 ppm sulfur. This added advantage is particularly important because of the increasing demand for sulfur-free fuels due to more stringent air pollution standards.

Combustion of the normally liquid synthetic fuels produced in the present invention results in a clean flue gas which does not need added clean-up to meet air pollution standards. Furthermore, the normally gaseous reaction products from the Fischer-Tropsch and hydrogenation steps are also essentially free of sulfur contaminants which also eliminate or reduce the need for flue-gas sulfur removal.

Hydrogenation catalysts useful in the present invention, generally comprise a composite of an oxide or other compound of a transition metal on an inorganic solid refractory metal oxide base, such as alumina. Well-known transition metals useful as hydrogenation catalysts include, in general, the Group VI-B metals, Group VIII metals, their oxides, sulfides, or mixtures thereof. Particularly preferred hydrogenation catalysts include the oxides of platinum, palladium, or rhodium deposited on a low or non-acidic refractory metal oxides.

Multifunctional catalysts can also be used in the present invention. By "multifunctional catalyst" is meant a catalyst which exhibits some other activity in addition to hydrogenation activity such as a hydrocracking catalyst which exhibits both hydrogenation and cracking activity. It is preferred to use a hydrocracking catalyst in the present invention, because in addition to converting the oxygenated components to hydrocarbons the use of the hydrocracking catalyst affords many other advantages including:

1. conversion of the high boiling hydrocarbons produced in the Fischer-Tropsch process to lower boiling hydrocarbons which boil in the range of 60° to 600° F which is particularly preferred for a turbine fuel;

2. increasing the yield of branched chain paraffins which have higher octane values than the normal olefins and paraffins which can comprise from 30 to 80 weight percent of the normally liquid hydrocarbons formed in the Fischer-Tropsch process. This feature of the invention is particularly useful where a portion of the normally liquid hydrocarbons might be used as a transportation fuel.

3. lowering of the cloud point or pour point of the liquid product by reducing the concentration of normal paraffins. This reduces or eliminates the necessity for heated storage tanks.

Hydrocracking catalysts for use in the present invention comprise a hydrogenation component and a cracking component. Preferably the hydrogenation component is supported on a refractory cracking base. Suitable cracking bases include, for example, two or more refractory oxides such as silica-alumina, silica-magnesia, silica-zirconia, alumina-boria, silica-titania, silica-zirconia-titania, acid-treated clays, and the like. Acidic metal phosphates such as alumina phosphate may also be used. Preferred cracking bases comprise composites of silica and alumina. Additionally, and particularly preferred for use in the present invention are the partially dehydrated zeolitic crystalline molecular sieves of the X or Y crystal type, having relatively uniform pore diameters of about 8–14 Angstroms and comprising silica, alumina, and one or more exchangeable zeolitic cations alone or in intimate admixture with other amorphous bases. Particularly preferred are cracking supports containing from 20 to 100 weight percent zeolite.

The hydrogenation components are present on the cracking support in an amount from 0.3 to 25 weight percent. Suitable hydrogenation components are selected from the Group VI-B metals Group VIII metals, their oxides, or mixtures thereof. Useful hydrogenation components comprise the oxides of chromium, tungsten, cobalt, nickel, cobalt or the corresponding free metals or any combination thereof. Particularly useful are the metals platinum, palladium, rhodium or iridium. The oxides of other transition metals such as rhenium can be used.

Hyrogenation reaction conditions include temperatures in the range 400°–800° F, preferably 400°–750° F, total pressures between 100–1000 psig, preferably 200–600 psig, partial pressures of hydrogen between 50–450 psig, preferably 150–360 psig, and GHSV's between 200–2000, preferably between 500–1500. Much higher total pressures and higher hydrogen partial pressures can be utilized, but the use of low pressures is particularly preferred, since this results in large savings in construction and operating costs.

An alternative to having separate reaction zones 18 and 21 is to have a single reaction zone containing both a hydrocarbon synthesis catalyst and a hydrogenation catalyst. A single reaction zone can be used containing a physical mixture of the two catalysts, or the catalysts can comprise two or more distinct layers in a single reaction zone, with the synthesis gas passing first over a layer of the hydrocarbon synthesis catalyst and subsequently over a layer of the hdyrogenation catalyst. Two reaction zones are preferred, however, so that one can readily maintain optimum reaction conditions for each reaction.

This element of the invention of hydrocracking the Fischer-Tropsch reaction product is more fully discussed in my concurrently filed application entitled "Hydrocracking the Presence of Water and a Low Hydrogen Partial Pressure", Ser. No. 586,673, filed June 13, 1975, the entire disclosure of which is incorporated herein by reference.

The effluent from the hydrogenation reaction zone is passed via line 23 into separation zone 25. The effluent will comprise primarily hydrocarbons, $H_2O$, $CO_2$, unreacted $H_2$ and CO, and small residual amounts of oxygenated components. The various components can be separated by conventional means, for example by distillation, but it is preferred to pass the effluent first though a condenser, separating the effluent into gaseous and liquid fractions. The condensed liquid fractions will phase-separate, with the hydrocarbons comprising one phase and water comprising the second phase. The liquid hydrocarbon phase will contain small residual amounts of water, which can be removed by conventional means. The normally liquid hydrocarbons are passed via line 27 to storage zone 29. The normally liquid hydrocarbon fraction makes an excellent turbine fuel, since it boils in the range 60° to 800° F, is essentially free of sulfur compounds ash, and oxygenated components. The water phase can be disposed of after removal of residual quantities of contaminants such as acetic acid, via line 26. Preferably, however, the water phase including any contaminants, is recycled to the gasifier 10 thus avoiding waste-water treatment costs and providing a means for recovery of the carbon-values of any contaminants. The $H_2$ in the gaseous fraction can be recycled to the hydrocracker after removal of at least a portion of the CO, $CO_2$ and any of the light uncondensed hydrocarbons such as methane and ethane. Also, all or portions of the light hydrocarbons formed in the Fischer-Tropsch or hydrocracking steps, for example, the $C_3$ and $C_4$ hydrocarbons, can be separated and used in other processes or can be reformed to produced $H_2$ and CO for recycle to the Fischer-Tropsch step. The $C_3$ and $C_4$ hydrocarbons can also be liquefied and stored under pressure and used as needed in the generation of additional power. Preferably, however, the gaseous fraction, 28, separated in separation zone 25, containing $H_2$, CO, $CO_2$ and light hydrocarbons such as methane, ethane, propane and butane, is combined with a portion of the synthesis gas from the gasifier via lines 14 or 16 and the combined gases are fed via line 30 to combustion zone 35, wherein the gases are combusted and the exothermic heat of reaction is used to generate steam, 31, which steam in turn is used to rotate steam turbine 32 to generate a base-load electrical power output. The combusted gases can, of course, be expanded through an open-cycle turbine rather than used to generate steam, but it is preferred to generate high-pressure steam since steam turbines are generally more efficient than open-cycle gas turbines.

A further advantage of the present invention resides in the fact that the combined gaseous stream, 30, has a higher Btu value than the synthesis gas above. The normally gaseous products, 28, from the paraffin synthesis and hydrogenation zones, contain high concentrations of high Btu-value hydrocarbons, particularly methane, ethane and propane, which increase the net Btu value of the combined gases. Thus, the paraffin synthesis and hydrogenation zones, in addition to producing a value liquid product useful for peak-load power demand, also serves the important function of increasing the Btu value of the gaseous fuel used for producing the base power load.

For peak-load power demand, the normally liquid hydrocarbons are passed via line 34 to combustion zone 36, wherein the liquid hydrocarbons are mixed with air and combusted, forming a clean flue gas. The flue gas then passes through expansion turbine 38 which in turn is coupled to an electrical generator which provides supplemental electrical power for peak-load power demand.

The energy in the exhausted flue gas can be recovered to increase the overall thermal efficiency of the process. The sensible heat in exhaust flue gas can be used to heat the air feed to combustion zones 35 or 36 or the exhaust flue gas can be utilized to generate additional steam for supply to the steam turbine 32 or as a feed to the gasifier 10. Illustrative regenerative and combined cycle gas turbine systems which can be used in the present invention are described, for example, in

*Electrical World*, June 1, 1974, pages 81–82, the disclosure of which is incorporated herein by reference.

Although various embodiments of the invention have been described, it is to be understood that they are meant to be illustrative only and not limiting. Certain features may be changed without departing from the spirit or scope of the invention. It is apparent that the present invention has broad application to the production of power from carbonaceous materials. Furthermore, it is readily apparent to one skilled in the art that portions of the gaseous and liquid hydrocarbon products can be used for other purposes, including transportation fuels. Accordingly, the invention is not to be construed as limited to the specific embodiments or examples discussed, but only as defined in the appended claims.

What is claimed is:

1. A process for the generation of power from a solid carbonaceous material which comprises:
   a. forming a combustible synthesis gas by reacting said carbonaceous material with steam and oxygen at an elevated temperature;
   b. passing a first portion of said synthesis gas into a reaction zone containing a hydrocarbon synthesis catalyst and a hydrogenation catalyst and forming a reaction product mixture containing water, $H_2$, CO, $CO_2$ and synthetic hydrocarbons;
   c. separating from said reaction product mixture a gaseous first fraction comprising $H_2$, CO, $CO_2$ and light hydrocarbons, a second fraction comprising normally liquid hydrocarbons and a third fraction comprising water;
   d. combining at least a portion of said first fraction with a second portion of said synthesis gas and combusting said combined gases and generating power from said combusted gases; and
   e. generating additional power from said liquid hydrocarbons by combusting at least a portion of said hydrocarbons forming a flue gas and passing said flue gas through an expansion turbine as the working fluid.

2. The process of claim 1 wherein said combined gases are combusted to generate steam and electrical power is generated from said steam by expanding said steam through a turbine coupled to an electrical generator.

3. The process of claim 1 wherein said power in steps (d) and (e) is electrical.

4. The process of claim 1 wherein said synthesis gas comprises $H_2$ and CO and the ratio of $H_2$ to CO is in the range 0.75:1 to 3:1.

5. The process of claim 1 wherein said hydrogenation catalyst comprises a Group VIII metal deposited on a low or non-acidic refractory metal oxide.

6. The process of claim 1 wherein said hydrogenation catalyst is deposited on a cracking support containing zeolite.

7. The process of claim 1 wherein said reaction zone contains a first layer of a hydrocarbon synthesis catalyst and a second layer of a hydrocracking catalyst and the volume ratio of said hydrocarbon synthesis catalyst to said hydrocracking catalyst is in the range 10/1:1/2.

8. The process of claim 7 wherein said hydrocarbon synthesis catalyst comprises an iron-copper catalyst and said hydrocracking catalyst comsprises palladium deposited on a cracking support containing zeolite.

9. The process of claim 1 wherein said carbonaceous material is coal.

10. The process of claim 1 wherein said synthesis gas also contains $CO_2$, $H_2S$ and $NH_3$, and substantially all of said $CO_2$, $H_2S$ and $NH_3$ are separated from said synthesis gas.

* * * * *